United States Patent [19]

Green et al.

[11] Patent Number: 4,612,815

[45] Date of Patent: Sep. 23, 1986

[54] METHOD AND APPARATUS FOR SAMPLING HAZARDOUS MATERIAL

[76] Inventors: Dennis A. Green, 4835 E. Kachina Trail #5, Phoenix, Ariz. 85044; Thomas L. Purcell, 8737 E. Hubbell St., Scottsdale, Ariz. 85257

[21] Appl. No.: 701,390

[22] Filed: Feb. 14, 1985

[51] Int. Cl.$^4$ .............................................. G01N 1/14
[52] U.S. Cl. ................. 73/864.11; 73/864.51
[58] Field of Search ........... 73/864.01, 864.11, 864.16, 73/864.34, 864.51, 864.63

[56] References Cited

U.S. PATENT DOCUMENTS

| | | | |
|---|---|---|---|
| 1,016,830 | 2/1912 | Jack | 417/903 |
| 1,736,392 | 11/1929 | Coss et al. | 73/864.16 |
| 2,057,398 | 10/1936 | Sperling | 73/864.51 |
| 2,751,787 | 6/1956 | Porter | 73/864.63 |
| 3,062,056 | 11/1962 | Wicoff | 73/864.34 |

*Primary Examiner*—Stewart J. Levy
*Assistant Examiner*—Robert R. Raevis
*Attorney, Agent, or Firm*—Harry M. Weiss & Associates

[57] ABSTRACT

Apparatus for sampling a material in a container both in a laboratory environment and in a field environment is shown. The apparatus includes a portable pump for generating either a partial pressure with respect to atmosphere or a partial vacuum with respect to atmosphere. The partial vacuum is used to force the material from the container through a collection tube into a specimen bottle. When the material in the container is too viscous to be directly drawn into the specimen bottle, a pressure is applied to one end of the collection tube and the material in the collection tube is driven into the specimen bottle. The footpump is modified to provide both a pressure and a vacuum nozzle and is easily portable to a remote location site.

6 Claims, 6 Drawing Figures

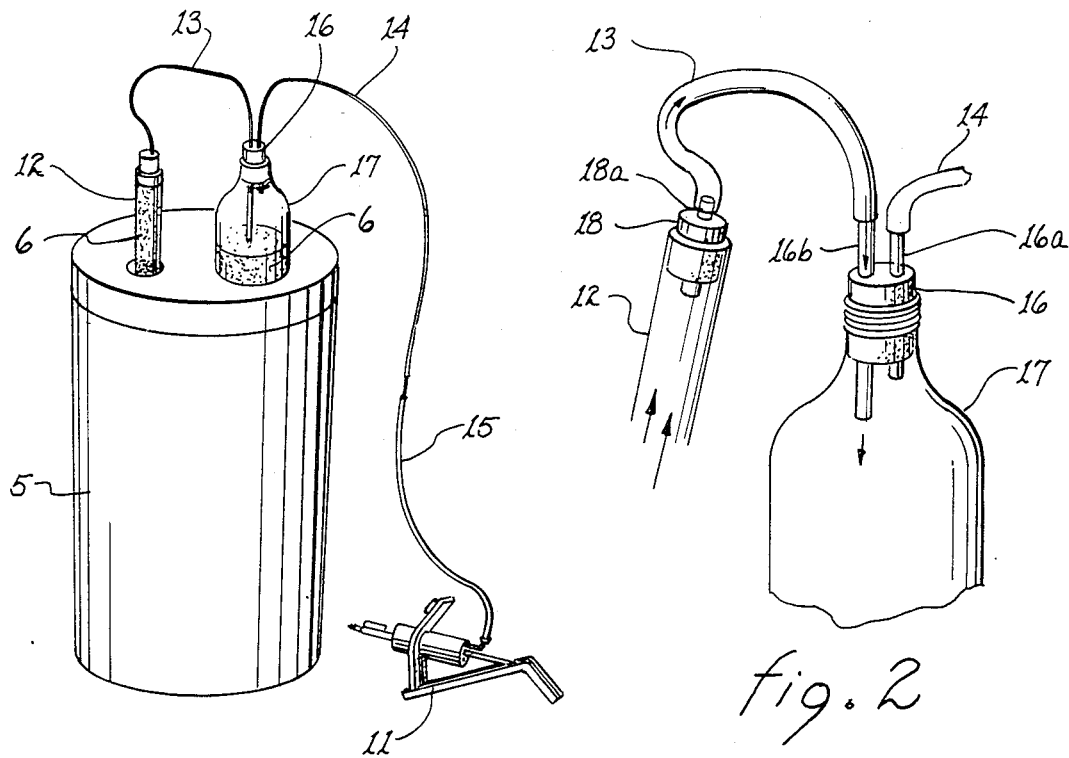
fig. 1
fig. 2
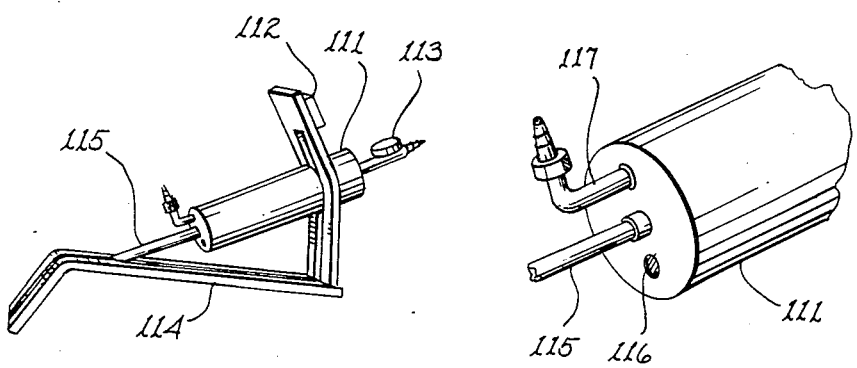
fig. 3a
fig. 3b

METHOD AND APPARATUS FOR SAMPLING HAZARDOUS MATERIAL

BACKGROUND OF THE INVENTION

1. Field of the Invention

This invention relates generally to sampling of unknown materials and, more particularly, to the sampling of materials in a container that may include hazard components. 2. Discussion of the Related Art As concern for the impact on the environment of toxic materials has increased, more emphasis has been placed on the analysis of the unknown and potentially dangerous materials. In a time of less concern for environmental problems and less sophistication concerning the lasting effects of any pollutants, a typical procedure was to store or possibly bury materials at a remote location, frequently in unmarked containers. Typically, little effort was expended in segrating toxic material from mere waste material, or indeed in providing even a rough inventory of contents. Even at the present time, many smaller entities do not understand the nature of problems of many materials in the environment and/or are reluctant or unable to dispose of the water materials in an approved manner.

As a result of these and other factors, storage facilities or disposal sites frequently have an inventory of containers for which little or no information with respect to the contents are available. Bacause testing of the materials frequently involves complex analysis, particularly as improved testing methods have been, extended the list of potentially dangerous materials, samples must be extracted from the containers and these samples are taken to the test facilities.

The procedure is complicated by the fact that the storage or disposal sites can be remote sites and can involve the handling of unknown and possible extremely dangerous materials. Thus, the apparatus that can be transported to the site at which samples are to be taken must be portable, and yet must be effectively designed to protect the operator.

A further problem can arise because many of the uninventoried containers can be several years in age and, consequently, changes may have taken place in the properties of the material. For example, the viscosity of the material can be changed causing the introduction into a specimen container difficult. Similarly, a separation of the material into layers can have occurred so that a sample of a particular portion, such as the material in the bottom of the container, can be deceptive.

In the past, specimens have typically been gathered by having a specimen container, such as a tube, into which specimen material is introduced. By releasing a stopper at the bottom of a tube, specimen material can be admitted at the entrance. This technique suffers from several defects. Control of the entrance of the material to the specimen tube can be difficult and often impossible for materials with a high viscosity properties. Furthermore, the elaborate controllable tubes, after collecting specimen material must thereafter be maintained, at least temporarily, for the storage of the specimen material.

A need has therefore been felt for a procedure and apparatus that can be used to obtain specimen samples from containers. The procedure should accommodate a wide range of viscosities of the specimen material, can obtain specimen containers, and for which the resulting specimen holders are inexpensive.

SUMMARY OF THE INVENTION

It is an object of the present invention to provide an improved procedure and apparatus for collection of specimen samples from containers.

It is a further object of the present invention to provide improved apparatus and method for removing samples from a waste container and store the sample in a specimen holder.

It is a still further object of the present invention to provide apparatus and method for removing specimen material from a container with minimum possibility of exposure to the material.

It is a more particular object of the present invention to provide apparatus and method for transferring liquid material by creating a vacuum for moving the material into a specimen holder.

The aforementioned and other objects are accomplished, according to the present invention, by a foot operated vacuum pump, a specimen bottle and a collection tube. The collection tube is placed into the container, and one end of the tube is coupled to the vacuum pump. When the pump is activated, the vacuum formed by the pump provides a pressure that draws up the waste material into the specimen jar through the pressure exerted by the vacuum formed with the pump. The pump is operated by a foot and is easily transportable. In those cases where the waste in the container is viscous and cannot be drawn through the tube can be filled with the waste material and the pressure part of the pump can be coupled and the toxic material will be forced out of the specimen tube into the specimen bottle. The pump is a commercially available pump modified to provide a vacuum as well as the normal pressure component.

These and other features of the invention will be understood upon reading of the following description along with the drawings.

BRIEF DESCRIPTION OF THE FIGURES

FIG. 1 shows the arrangement of the parts of the invention for extracting waste material from a container.

FIG. 2 shows how the specimen bottle is coupled to the collector tube and to the pump.

FIG. 3 is drawing of the pump showing the pieces of the pump and the modifications according to the present invention.

DESCRIPTION OF THE PREFERRED EMBODIMENT

Detailed Description of the Figures

Figure 4:
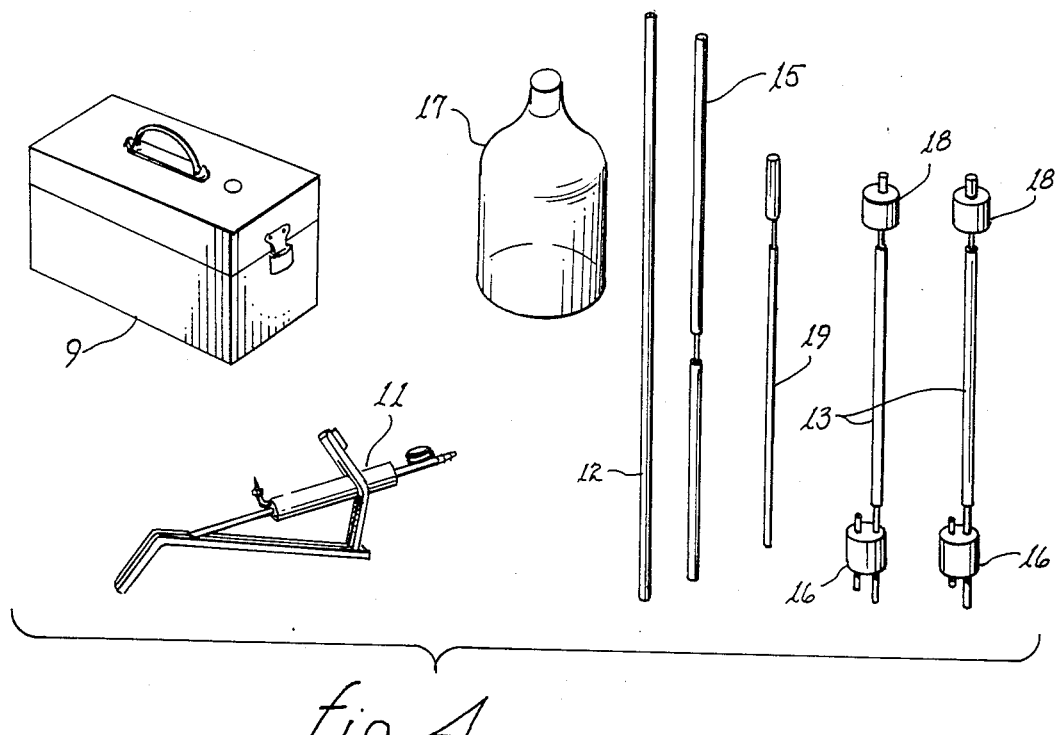
FIG. 4 shows the apparatus necessary to practice the present invention.

Referring now to FIG. 1, the container 5 holds an unknown and potentially dangerous material. The material shown in FIG. 1 as substance 6 is drawn through the collection tube 12 and through connecting tube 13 to the sample specimen holder 17. Connecting tubes 14 and 15 are coupled to a footpump 11.

Referring next to FIG. 2, the method of coupling the collection tube and the pump to the specimen holder is shown. A stopper 18 with a conduit 18a therethrough, is placed into one end of collection tube 12. Conduit 18a has a plastic tubing 13 coupled thereto at one end and the other end is coupled to tube 16b passing through stopper 16. Stopper 16 also has tube 16a passing therethrough and stopper 16 is inserted into the mouth of the collection bottle. The tube-16a is coupled to connecting tubing 14 which is ultimately coupled to the vacuum pump 11 (not shown).

Referring next to FIG. 3a, the pump used in the instant invention is shown. The pump includes the pressure housing 111, the base 114, a piston 115 coupled to the interior of housing 111 and coupled to the base 114. Foot pedal 112 when depressed causes the piston associated with element 115 to force gas out through the pressure gage/nozzle element indicated by 113 in the figure. In FIG. 3b, the end of the footpump housing 111 is shown. In the commercially available footpumps, two apertures are available around the piston conecting member 115. In the preferred embodiment, one of these apertures is covered and the other aperture has inserted therein a nozzle 117.

Referring next to FIG. 4, the apparatus necessary for collection of samples from toxic waste containers are shown. Carrying case 9 can be used to transport the foot pump 11. Needed for the extraction of waste materials from containers, is a sample bottle 17 into which the waste sample can be collected. The vacuum pump-sample bottle connecting tube 15 is used to couple the pump and the sample bottle. Pressure outlet valve connecting tube 19 is used to apply pressure to the collection tube and is coupled to the pressure nozzle of the footpump. Connecting tubes 13 connect the collection bottle into which the stopper 18 is inserted with the specimen bottle into which stopper 16 is inserted.

Figure 5:
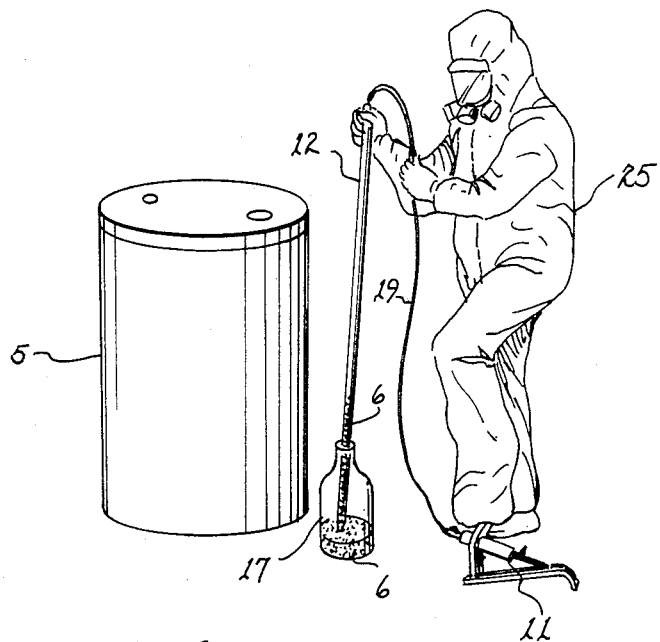
FIG. 5 shows how the apparatus can be used to remove viscous materials from the collection tube.

Referring next to FIG. 5, a specimen sample has been removed from container 5 and is now in collection tube 12. When the sample 6 is highly viscous the coupling 19 is coupled to the pressure valve of footpump 11 and to the free end of collection tube 12. As the operator operates the footpump 11, the pressure built up in connecting tube 19 and in collection tube 12 forces the specimen material 6 into the specimen bottle 17.

Operation of the Preferred Embodiment

The inventive apparatus is meant to be used in both the laboratory environment and in the field environment. Thus, the apparatus must be both sturdy and must be easily transportable. The containers from which samples must be extracted are typically at remote locations and the apparatus must be carried thereto. In addition, the apparatus must be easy to assemble and to disassemble, and because of the constant exposure to toxic/hazardous materials, the components must be relatively inexpensive so that they can be discarded after a relatively short period of time.

The operation of the apparatus entails using the pump 11 to generate a partial vacuum in the specimen bottle 17 and in the collection tube 12. The partial vacuum, in conjunction with the atmospheric air pressure pressing on the surface of the toxic material, forces the material into the collection tube 12. When the waste material does not have a high viscosity, then the material is drawn through the collection tube 12 into the connecting tube 13 and into the specimen bottle 17. In the specimen bottle 17, the waste material falls to the bottom of the specimen bottle and a vacuum is maintained in the specimen bottle and consequently in the connecting tube 13 and collection tube 12. After a sufficient quantity of material is collected in the specimen bottle 17, then the apparatus can be easily disassembled into its components and the connecting tube 13, stopper 18, tube 18a and the collection tube 12 and stopper 16 and associated tubes can either be discarded or can be cleaned.

As shown in FIG. 5, when the material is too viscous to be drawn by the partial vacuum available through the footpump through connecting tube 13, then the pressure portion of the pump can be used to force the viscous material from the collection tube into the specimen bottle.

It will be clear that with only slight modifications, the disclosed apparatus can be used to obtain sample material even from large underground tanks where utilizing a collection tube 12 of sufficient length an be difficult. If a flexible tube material is used, a weight can be coupled to an end of the tube and the weight and the tube dropped into the tank. Using the partial vacuum generated by the footpump, specimen material can be drawn into the sample jar. It will also be clear that by varying the height of the tube, the materials at various levels can be sampled.

The above description is included to illustrate the operation of the preferred embodiment and is not meant to limit the scope of the invention. The scope of the invention is to be limited only by the following claims. Many variations will be apparent to those skilled in the art that would yet be encompassed by the spirit and scope of the invention.

What is claimed is:

1. Portable apparatus for sampling material in a container comprising:
    a foot-operated pump capable of generating both a partial vacuum less than atmospheric pressure and a pressure exceeding atmospheric pressure;
    a specimen bottle;
    a collection tube for insertion into the container containing the material to be sampled;
    means for coupling the collection tube and the specimen bottle; and
    means for coupling said foot-operated pump to said specimen bottle.

2. The apparatus obtaining a sample of material from a container of claim 1 wherein said pump can be coupled to said collection tube for forcing said material out of said collection tube.

3. The apparatus for sampling material in a container of claim 1 wherein said collection tube is a flexible tube with a weight coupled in a vicinity of an end of said collection tube to be immersed in said material.

4. The apparatus for sampling material in a container of claim 1 wherein said foot-operated pump is a portable pump for providing pressure greater than atmospheric pressure in first chamber, said pump modified to restrict a flow of air into a second chamber, said second chamber providing a pressure below atmospheric pressure in said chamber where said pump is operated.

5. A method of sampling a fluid material in a container, comprising the steps of:
    inserting a collection tube into said container;
    applying a partial vacuum to said collection tube, said material being drawn into said collection tube;
    applying above atmospheric pressure to said collection tube with an end inserted in a sample holder, said pressure causing at least a portion of said material in said collection tube to be entered into said sample holder; and thereafter converting a foot-operated pump into a foot-operated device for providing both a pressure above atmospheric pressure and a pressure below atmospheric pressure, said pumps utilized to provide said partial vacuum.

6. A method of sampling a fluid material in a container, comprising the steps of:

inserting a collection tube into said container;
applying a partial vacuum to said collection tube, said material being drawn into said collection tube, said step of applying a partial vacuum to said collection tube includes the step of utilizing a foot-operated pump converted to produce a partial vacuum.

* * * * *